United States Patent [19]

Imran

[11] Patent Number: 5,449,381
[45] Date of Patent: Sep. 12, 1995

[54] ENDOCARDIAL CATHETER FOR DEFIBRILLATION, CARDIOVERSION AND PACING, AND A SYSTEM AND METHOD UTILIZING THE SAME

[76] Inventor: Mir Imran, 731 Barron Ave., Palo Alto, Calif. 94306

[21] Appl. No.: 22,818

[22] Filed: Feb. 24, 1993

Related U.S. Application Data

[63] Continuation of Ser. No. 657,169, Feb. 15, 1991, abandoned.

[51] Int. Cl.6 ............................................. A61N 1/05
[52] U.S. Cl. ..................................................... 607/122
[58] Field of Search ............... 128/786, 642, 419 P, 128/419 D, 658; 607/5, 116, 119, 122, 123, 125

[56] References Cited

U.S. PATENT DOCUMENTS

| | | | |
|---|---|---|---|
| 4,590,946 | 5/1986 | Loeb | 128/642 |
| 4,664,120 | 5/1987 | Hess | 128/419 P X |
| 4,699,147 | 10/1987 | Chilson et al. | 128/786 X |
| 4,807,626 | 2/1989 | McGirr | 128/658 X |
| 4,940,064 | 7/1990 | Desai | 128/786 X |
| 5,010,894 | 4/1991 | Edhag | 128/786 X |
| 5,095,905 | 3/1992 | Klepinski | 128/642 |
| 5,111,811 | 5/1992 | Smits | 128/786 X |
| 5,117,828 | 6/1992 | Metzger et al. | 128/786 X |

Primary Examiner—Lee S. Cohen
Assistant Examiner—Samuel Gilbert
Attorney, Agent, or Firm—Flehr, Hohbach, Test, Albritton & Herbert

[57] ABSTRACT

Endocardial catheter for introduction into a lumen of a vessel leading to a chamber formed by the wall of a heart of a patient comprising a flexible elongate tubular member having proximal and distal extremities and having a longitudinal axis. An electrode having radially spaced apart electrode portions is provided. An expandable device movable between contracted and expanded positions is secured to the distal extremity of the flexible elongate tubular member. The expandable device has an outer surface upon which the electrode is mounted. An elongate element is secured to the expandable device for moving the expandable device to the expanded position to thereby move the electrode into engagement with the wall forming the chamber of the heart. An additional electrode is mounted on the flexible elongate tubular member in relatively close proximity to the first named electrode. Leads are connected to the electrode and to the additional electrode and extend to the proximal extremity of the flexible elongate member.

10 Claims, 1 Drawing Sheet

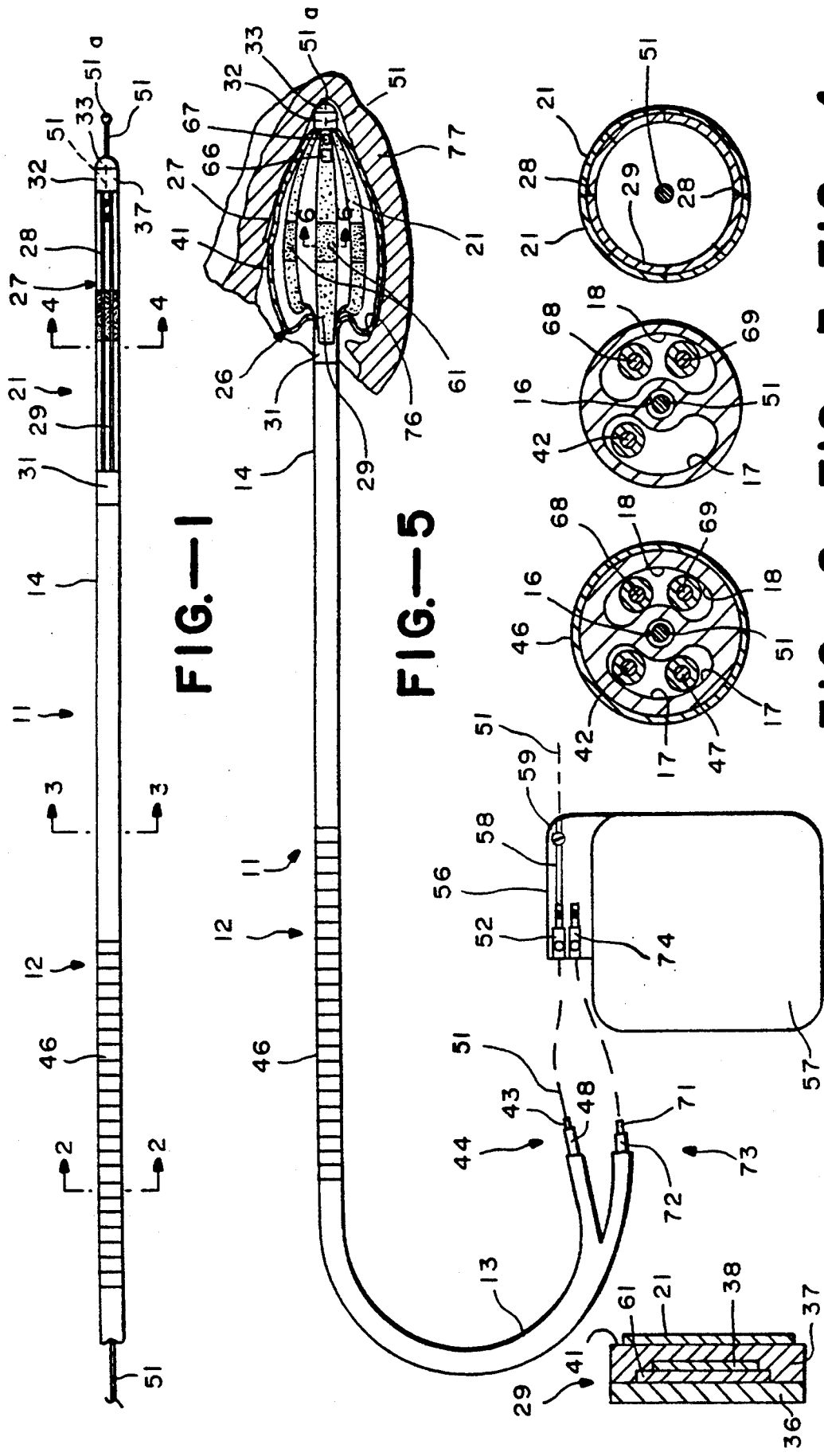

ENDOCARDIAL CATHETER FOR DEFIBRILLATION, CARDIOVERSION AND PACING, AND A SYSTEM AND METHOD UTILIZING THE SAME

This is a continuation of application Ser. No. 07/657,169 filed Feb. 15, 1991, now abandoned.

This invention relates to an endocardial catheter for delibrillation, cardioversion and pacing and a system and method for utilizing the same.

Heretofore endocardial catheters have been provided for delibrillation, cardioversion and pacing. Such catheters that are currently being used are primarily comprised of two spring electrodes with large surface areas. One resides in the right ventricle and the other over the right atrium and partially in the superior vena cava. Other catheters use one spring electrode in the right ventricle and an apical patch for the other electrode. Defibrillation and cardioversion is accomplished by supplying energy typically between 25 and 30 joules between the two electrodes.

Such electrode systems have the disadvantage that a substantial portion of the defibrillation or cardioversion energy is dissipated in the blood pool since the ventricular portion of the catheter is residing in the blood pool. It is desirable to have the electrode system make as intimate a contact as possible with the wall of the ventricle so that the loss of energy in the blood pool is minimized and to deliver most of the energy to the heart muscle to effect defibrillation or a cardioversion. This is an important consideration with implantable devices where it is desirable to reduce the energy requirements for cardioversion and defibrillation and thereby permit reduction in the size of the implantable device for defibrillation and/or cardioversion.

In general, it is an object of the present invention to provide an endocardial catheter for defibrillation, cardioversion and pacing and a system and method utilizing the same which provides a better distribution of energy to the heart muscle.

Another object of the invention is to provide a catheter system and method of the above character which reduces the energy losses in the blood pool in the chamber of the heart in which the distal extremity of the catheter is disposed.

Another object of the invention is to provide a catheter system and method of the above character in which the electrodes are placed in intimate contact with the wall of the chamber of the heart in which the distal extremity of the catheter is disposed.

Another object of the invention is to provide a catheter system and method of the above character which has substantially reduced power requirements for defibrillation and cardioversion.

Another object of the invention is to provide a catheter, system and method which includes bipolar electrodes to permit pacing and/or monitoring.

Additional objects and features of the invention will appear from the following description in which the preferred embodiments of the invention are set forth in detail in conjunction with the accompanying drawings.

FIG. 1 is a partial plan view of an endocardial catheter for defibrillation, cardioversion and pacing and/or monitoring incorporating the present invention with expandable means and showing the expandable means in a contracted position.

FIG. 2 is a cross-sectional view taken along the line 2—2 of FIG. 1.

FIG. 3 is a cross-sectional view taken along the line 3—3 of FIG. 1.

FIG. 4 is a cross-sectional view taken along the line 4—4 of FIG. 1.

FIG. 5 is a side elevational view showing the catheter in FIG. 1 disposed within the right ventricle of a human heart with the expandable means in an expanded position and adjusted to be connected into a system of the present invention.

FIG. 6 is a pre-enlarged cross-sectional view taken along the line 6—6 of FIG. 5.

In general, the endocardial catheter for defibrillation, cardioversion, pacing and/or monitoring is for introduction into a lumen of a vessel leading to the heart and to be moved into engagement with a wall of the heart. It consists of a flexible elongate tubular member having proximal and distal extremities. Electrode means is provided which has radially spaced apart electrode portions. Flexible expandable means having an outer surface is provided which is movable between contracted and expanded positions and is secured to the distal extremity of the flexible elongate tubular member. Means is provided for securing the electrode means to the outer surface of the expandable means. Means is secured to the expandable means for moving the expandable means to the expanded position to move the electrode means carried thereby into engagement with a wall of the heart when the expandable means is disposed within the heart. A spring like electrode is mounted on the exterior of the flexible elongate tubular member in relatively close proximity to the electrode means. Lead means is connected to the electrode means and to the spring-like electrode and extends to the proximal extremity of the flexible elongate member.

As shown more particularly in FIG. 1, the endocardial catheter 11 for defibrillation, cardioversion, pacing and/or monitoring consists of a flexible elongate tubular member 12 having a longitudinal axial and being formed of a suitable plastic such as polyethylene. It is provided with proximal and distal extremities 13 and 14. Typically, it can have a length ranging from 120–150 cm. and a diameter of 8 to 10 French or a diameter of approximately 0.125". The tubular element 12 is provided with at least one lumen and as shown in FIGS. 2, 3 and 4 is provided with a central lumen 16 which extends axially of the flexible elongate element 12 and two substantially crescent shaped lumens 17 and 18 disposed on opposite sides of the central lumen 16.

Electrode means 21 is provided which has radially spaced apart electrode portions. Expandable means 26 is provided which is movable between contracted and expanded positions and is secured to the distal extremity of the flexible elongate tubular member 12. The expandable means 26 consists of a cylindrical member 27 which can be formed in a manner similar to that described in co-pending application Ser. No. 07/656,764, filed Feb. 15, 1991, now U.S. Pat. No. 5,156,151. As described therein, the cylindrical member 27 is provided with a plurality of parallel longitudinally extending slits 28 which form a plurality of parallel longitudinally extending elements or arms 29 that have proximal and distal extremities which are formed integral with or are attached to proximal and distal end portions 31 and 32. As described in said co-pending application, the end portions 31 and 32 are wrapped around a proximal mandrel (not shown) and a distal mandrel 33 and bonded thereto.

The arms 29 are formed in the manner described in said co-pending application Ser. No. 07/656,764, filed Feb. 15, 1991, now U.S. Pat. No. 5,156,151, of polyimide insulating layers 36 and 37 having embedded therein metal strips 38 (see FIG. 6) to create desired bowed conformation for the arms when the expandable means 26 is expanded.

The arms 29 have outer surfaces 41 on which there is provided metalization to form the electrode means 21 adherent thereto. This metallization can be in an appropriate form, as for example a multilayer metal structure such as copper coated with nickel and with the nickel coated with gold. The metallization providing the electrode means 21 covers substantially all of the outer surfaces 41 of the arms 29. The electrode means 21 converges at the proximal end portion and is connected to a single insulated conductor 42 which extends through the lumen 17 to the proximal extremity 13 and is secured to the center conductor 43 of a male coaxial connector 44. Another electrode 46 is provided on the flexible elongate tubular member 12. This electrode 46 can be formed of a suitable material such as a titanium helical spring which is wound tightly onto the elongate tubular member 12 in a position which is in relatively close proximity to the electrode means 21. Typically, it should be positioned so that it lies in the superior vena cava of the heart when the electrical means 21 is positioned in the right ventricle of the heart. As for example approximately 2" from the distal extremity of the electrode 46 to the proximal extremity of the electrode means 21. The electrode 46 typically can be in the form of a ribbon having a thickness of 0.018 to 0.020" and a width of 0.06". It has a suitable surface area for example 10-20 cm$^2$. A lead or conductor 47 is provided in the lumen 17 which is connected to the electrode 46 in the same manner as previous leads have been connected to the other electrodes. Lead 47 is connected to the outer conductor 48 of the male coaxial connector 44.

Means is secured to the expandable cylindrical member 27 for moving the expandable means 26 to the expanded position by causing the proximal and distal extremities of the cylindrical member 27 to move towards each other by causing the distal extremities to move towards the proximal extremity and consists of a pull wire 51 which extends through the center of the center conductor 43 of the coaxial connector 44 and into the central lumen 16 and through the proximal mandrels (not shown) and the distal mandrel 33. The pull wire 51 is provided with an enlargement 51a on its distal extremity so that when the pull wire 51 is pulled rearwardly its seats within the distal mandrel 33 and causes the distal extremity of the cylindrical member 27 to be pulled towards the proximal extremity and to cause the arms 29 carrying the electrode means 21 to be bowed outwardly into engagement with the wall of the heart forming the chamber of the heart in which the electrode means is disposed.

The coaxial connector 44 is adapted to be connected into a female coaxial connector 52 mounted in a header 56 of a conventional AICD (automatic implantable cardioversion defibrillator) 57. The header 56 is provided with a bore 58 which is in alignment with the female connector 52 and through which the pull wire 51 can extend. It is also provided with set screw 59 which is adapted to engage the pull wire 51 after the pull wire 56 has been tensioned in the manner hereinafter described.

Radiopaque markers 61 are provided on the expandable means 26 to aid in determining the amount of expansion of the expandable means 26. As shown in FIG. 5, these radiopaque markers 61 are spaced apart radially in the same longitudinal positions on the flexible elongate member 12 to form a circle. These markers can be formed of a suitable radiopaque metal such as lead, platinum or tungsten. It is preferable that these markers be of a size as for example 0.040" by 0.3" and a suitable thickness so that they are readily visible during fluoroscopy. This can be accomplished by utilizing thin sheets of lead or platinum and embedding them between the polyimide layers 36 and 37 and underlying the stripes 38 (see FIG. 6).

First and second bipolar electrodes 66 and 67 are provided on the expandable means 26 and as shown are disposed on the outer surface 41 of one of the arms 29 and are spaced apart longitudinally thereof where the electrode means 21 is not present. These bipolar electrodes 66 and 67 are connected to a pair of conductors 68 and 69 which if desired can be in the form of printed circuit leads provided on the inside surface of the arm 32 on which the electrodes 66 and 67 are mounted and then connected to conductors 68 and 69 which extend through the lumen 18 provided in the flexible elongate member 12. They are then connected to the center and outer conductor 71 and 72 of a male coaxial connector 73. The male connector 73 is adapted and received by a female connector 74 provided in the header 56.

Operation and use of the catheter 11 in conjunction with the system shown in FIG. 5 for performing the present invention may now briefly be described as follows. Let it be assumed that it is desired to carry out certain operations in the heart of a patient by use of a catheter 12 shown in FIG. 5. The catheter 11 as shown in FIG. 1 with the expandable means in a contracted position is introduced into a lumen of a vessel in the patient, as for example into the femoral and then advanced into the heart in a conventional manner during fluoroscopy so that the expandable means is positioned in a desired chamber in the heart as for example the right ventricle 76 as shown in a portion of the heart 77 of a human. After the expandable means 26 is within the right ventricle, the expandable means 26 can be expanded to its expanded position by pulling on the pull wire 51 and causing the distal extremity of the expandable cylindrical member 22 to be moved toward the proximal extremities cause the arms 29 to bow outwardly and thereby cause the electrode means 21 carried thereby to be moved into engagement with the wall of the heart forming the right ventricle.

The AICD device 57 can then be placed in the abdomen of the patient in a conventional manner with the catheter 11 being placed beneath the skin and extending into the heart. The pull wire 51 is tensioned to the desired amount. The set screw 59 is then tightened and thereafter the excess wire of the pull wire 51 extending from the header 56 is cut off.

The catheter 11 of the present invention can then be utilized for performing defibrillation and cardioversion by delivery of energy from the AICD device 57 to the two electrodes formed by the electrode means 21 and by the electrode 46. The energy is delivered asynchronously with respect to the electrical activity of the heart for defibrillation and in synchronization with the electrical activity as for example the R-wave of the heart for cardioversion. The energy delivered to the electrode means 21 and the electrode 46 typically is in the range of 700–800 volts and is applied through the high voltage leads 42 and 47.

The catheter 11 of the present invention can also be utilized for pacing and monitoring. This is accomplished by utilizing the closely spaced bipolar electrodes 66 and 67 carried by the expandable means 26 and in contact with the wall forming the chamber of the heart in which the expandable means 26 is disposed. The two closely spaced electrodes 66 and 67 make it possible to obtain a very noise-free R-wave signal that can be utilized for monitoring the heart and ascertaining when an arrhythmia is occurring. When it is ascertained that pacing is desired, a signal is supplied from the AICD 57 to the bipolar electrodes 66 and 67. Thus, it can be seen that the bipolar electrodes 66 and 67 can be utilized for monitoring as well as for pacing.

The expandable means 26 utilized in conjunction with the catheter 11 has the additional advantage in that because of the spacing of the arms, the expandable means does not interfere with the normal flow of blood into and out of the chamber in which it is disposed.

In connection with the catheter of the present invention, it should be appreciated that the expandable means can take various forms as for example, the spiral type form disclosed in co-pending application Ser. No. 07/656,764, filed Feb. 15, 1991, now U.S. Pat. No. 5,156,151. As disclosed therein, the outer surface of the spiral can be provided with electrode means 21 in the same manner as the arms 29 and that this electrode means can be moved into engagement with the wall forming the chamber of the heart in the same manner as the arms 29 carrying the electrode means 21 move the electrode means 21 into engagement with the wall forming the chamber of the heart in which the electrode means is disposed. The bipolar pacing and/or monitoring electrodes 66 and 67 can also be positioned on expandable means of this type.

Advantages of the catheter constructions of the present invention is that the electrodes are placed in intimate contact with the wall forming the chamber of the heart in which the distal extremity of the catheter is disposed. Energy delivered to the electrodes is delivered directly into the heart tissue with a minimum of the energy going into the blood passing through the chamber of the heart. Since a greater efficiency is achieved, less power need be delivered to the electrodes. The reduced power required makes it possible to substantially reduce the size of the AICD. Because of this increased efficiency, it is possible to reduce the size of the AICD. The expandable means utilized in conjunction with the catheter provides an additional advantage for the catheter. The spacing between the arms of the expandable means permits normal flow of blood into and out of the chamber in which it is disposed with a minimum of interference.

What is claimed is:

1. An endocardial catheter for introduction into a lumen of a vessel leading to a chamber formed by a wall of a heart of a patient and having a blood pool therein, the catheter comprising a flexible elongate tubular member having proximal and distal extremities and having a longitudinal axis, an electrode assembly having a plurality of radially spaced apart electrodes suitable for defibrillation and cardioversion, a support movable between contracted and expanded positions secured to the distal extremity of the flexible elongate tubular member, said support being comprised of elongate elements which are substantially rectangular in cross section and each including a layer of insulating material having an outer surface which is only adapted to face toward the wall of the chamber, means for securing said electrodes solely to said outer surfaces of said layers of insulating material adapted only to face toward the wall of the chamber, means secured to said support for moving said support to said expanded position to thereby move the electrodes into engagement with the wall forming the chamber of the heart whereby the electrodes will contact only the wall of the heart and will be out of substantial contact with the blood pool in the chamber, an additional electrode mounted on the flexible elongate tubular member in relatively close proximity to said electrode assembly and leads connected to the electrode assembly and to the additional electrode and extending to the proximal extremity of the flexible elongate member.

2. A catheter as in claim 1 together with radiopaque markers mounted on said support and underlying said electrode assembly and spaced apart radially of the support.

3. A catheter as in claim 2 wherein said radiopaque markers are disposed circumferentially.

4. A catheter as in claim 1 wherein said support has a distal extremity and wherein said means for moving said support to the expanded position includes a pull wire connected to the distal extremity of the support.

5. A catheter as in claim 4 wherein said pull wire extends to the proximal extremity of the flexible elongate member.

6. A catheter as in claim 1 together with first and second bipolar electrodes mounted in close proximity on one of the elongate elements and leads connected to the bipolar electrodes and extending to the proximal extremity of the flexible elongate member.

7. A catheter as in claim 1 wherein said electrodes cover a substantial portion of the outer surfaces of said layers of insulating material.

8. A system for defibrillation and cardioversion in a heart of a patient having a chamber formed by a wall and having a blood pool therein, the system comprising an endocardial catheter for introduction into the chamber and consisting of a flexible elongate tubular member having a proximal extremity and a distal extremity and having a longitudinal axis, an electrode assembly having radially spaced apart electrodes suitable for defibrillation and cardioversion, a support movable between contracted and expanded positions secured to the distal extremity of the flexible elongate tubular member, said support being comprised of elongate elements which are substantially rectangular in cross section and each including a layer of insulating material having an outer surface which is only adapted to face the wall forming the chamber, means for securing said electrodes solely to said outer surfaces of said layers of insulating material, means secured to said support for moving said support to said expanded position and to move the electrodes into engagement with the wall forming the chamber of the heart in which the support is disposed whereby the electrodes will contact only the wall of the heart and will be out of substantial contact with the blood pool in the chamber, an additional electrode carried by the flexible elongate tubular member in relatively close proximity to the electrode assembly, leads connected to the electrodes and to the additional electrode and extending to the proximal extremity of the flexible elongate member and an AICD device connected to said leads for supplying electrical energy to said leads.

9. A system as in claim 8 wherein said means secured to said support includes a pull wire and wherein said AICD device includes a bore through which the pull wire extends and means for securing the pull wire in a predetermined position in said bore with respect to said AICD device.

10. A system as in claim 8 together with first and second bipolar electrodes carried by the support, leads connected to the bipolar electrodes and extending to the proximal extremity of the flexible elongate member and means for connecting the leads connected to the bipolar electrodes to the AICD device.

* * * * *

UNITED STATES PATENT AND TRADEMARK OFFICE
CERTIFICATE OF CORRECTION

PATENT NO. : 5,449,381
DATED : September 12, 1995
INVENTOR(S) : Mir A. Imran

It is certified that error appears in the above-identified patent and that said Letters Patent is hereby corrected as shown below:

Title page, item [73], Assignee: should read--Cardiac Pathways Corporation, Sunnyvale, Calif.--.

Signed and Sealed this

Thirteenth Day of January, 1998

Attest:

Attesting Officer

BRUCE LEHMAN

Commissioner of Patents and Trademarks